(12) United States Patent
Stewart et al.

(10) Patent No.: US 7,783,006 B2
(45) Date of Patent: Aug. 24, 2010

(54) RADIATION TREATMENT USING X-RAY SOURCE

(75) Inventors: Daren L. Stewart, Belmont, CA (US); Paul A. Lovoi, Saratoga, CA (US); Thomas W. Rusch, Hopkins, MN (US); Alex Lim, Santa Clara, CA (US); Darius Francescatti, Barrington, IL (US)

(73) Assignee: Xoft, Inc., Sunnyvale, CA (US)

(*) Notice: Subject to any disclaimer, the term of this patent is extended or adjusted under 35 U.S.C. 154(b) by 975 days.

(21) Appl. No.: 10/962,247

(22) Filed: Oct. 8, 2004

(65) Prior Publication Data

US 2005/0080340 A1  Apr. 14, 2005

Related U.S. Application Data

(63) Continuation-in-part of application No. 10/683,885, filed on Oct. 10, 2003.

(51) Int. Cl.
*G21K 5/00* (2006.01)

(52) U.S. Cl. ............... 378/64; 600/1; 600/2; 600/3; 600/4; 378/65; 378/119

(58) Field of Classification Search .......... 600/1–8, 600/452, 459; 128/897–899; 378/65, 119
See application file for complete search history.

(56) References Cited

U.S. PATENT DOCUMENTS

| | | | |
|---|---|---|---|
| 4,530,840 A | 7/1985 | Tice et al. | |
| 4,767,628 A | 8/1988 | Hutchinson | |
| 4,891,225 A | 1/1990 | Langer et al. | |
| 4,906,474 A | 3/1990 | Langer et al. | |
| 4,957,744 A | 9/1990 | della Valle et al. | |
| 5,913,813 A | 6/1999 | Williams et al. | |
| 5,931,774 A | 8/1999 | Williams et al. | |
| 6,083,148 A | 7/2000 | Williams | |
| 6,413,204 B1 * | 7/2002 | Winkler et al. | 600/3 |
| 6,482,142 B1 | 11/2002 | Winkler et al. | |
| 6,871,758 B2 | 3/2005 | Berenshteyn | |
| 6,923,754 B2 | 8/2005 | Lubock | |
| 2003/0179854 A1 * | 9/2003 | Jaafar | 378/119 |

* cited by examiner

*Primary Examiner*—Brian Casler
*Assistant Examiner*—John F Ramirez
(74) *Attorney, Agent, or Firm*—Thomas M. Freiburger

(57) ABSTRACT

Methods and apparatus are described for irradiating living tissue via a cavity or lumen, using an inflatable balloon applicator. In a preferred embodiment the applicator balloon has a balloon skin with x-ray contrast material in relatively low concentration, so that an outline of the balloon will appear sharply when imaged externally. In another preferred embodiment the balloon catheter has a drain for withdrawing liquids from the cavity, which may include channels or texture on the exterior of the balloon. Methods are described for using a switchable miniature x-ray tube, variable as to voltage and current, to achieve accuracy in an isodose profile.

29 Claims, 4 Drawing Sheets

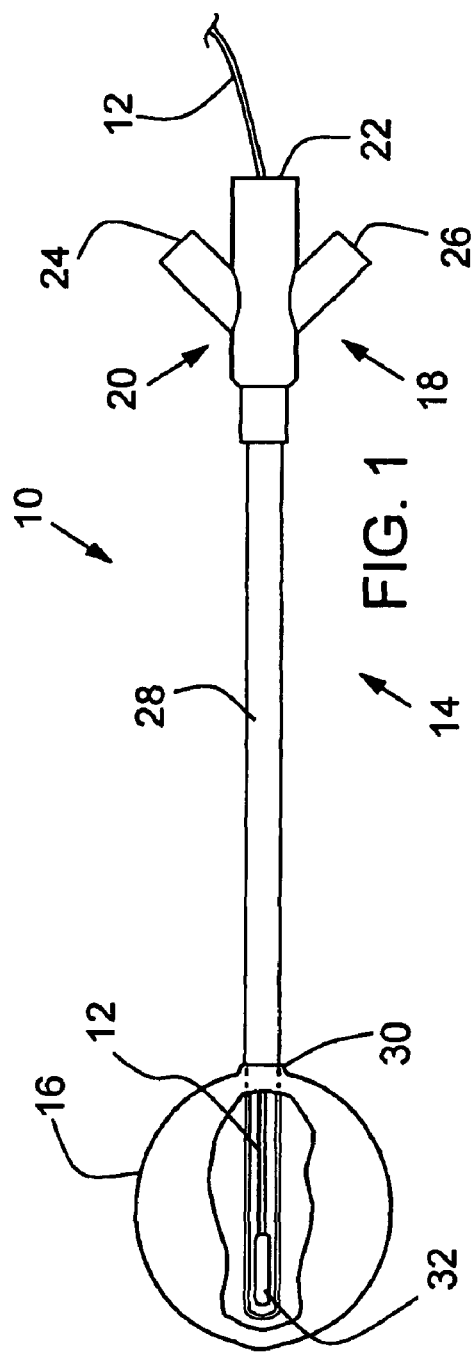
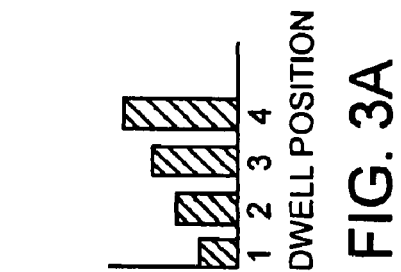
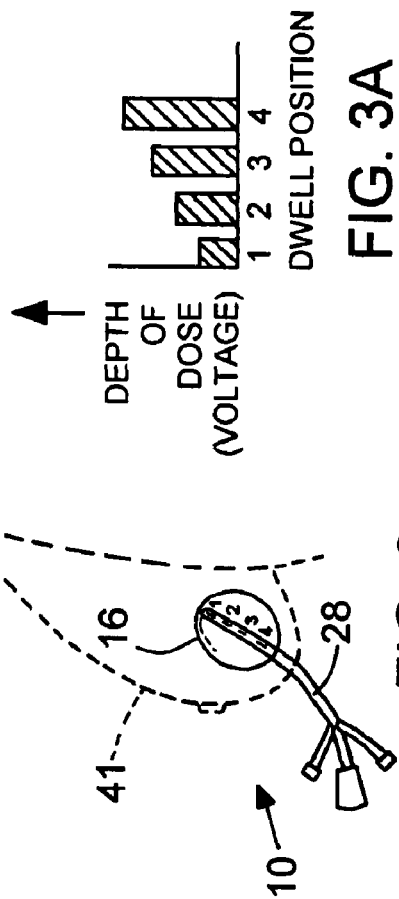

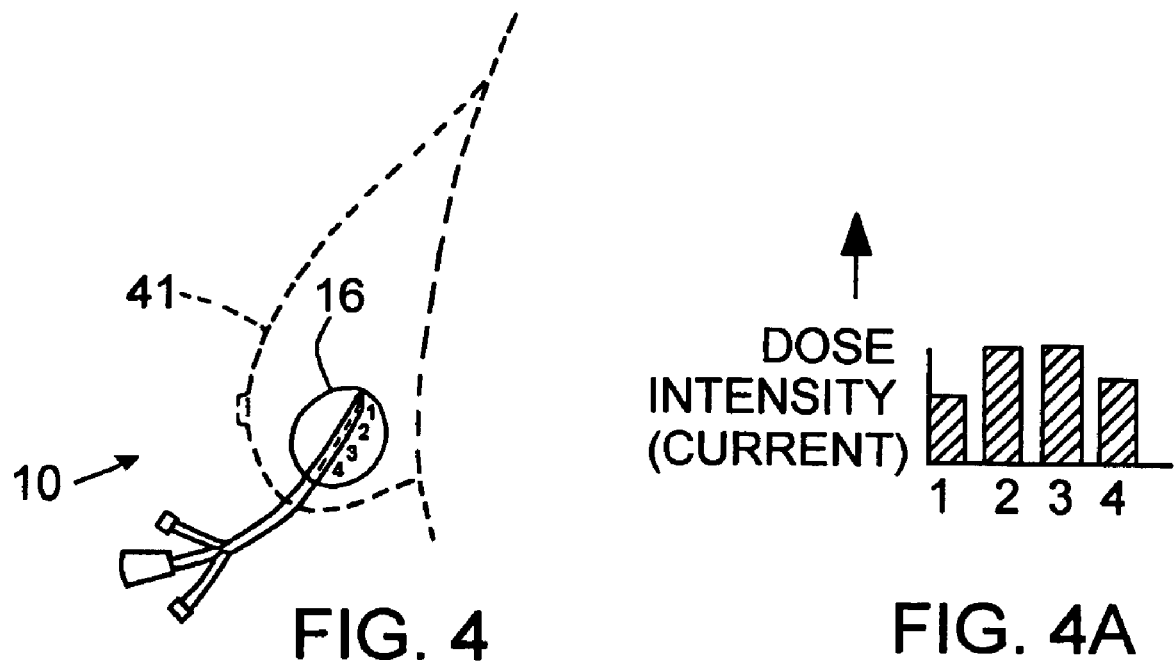
FIG. 4
FIG. 4A
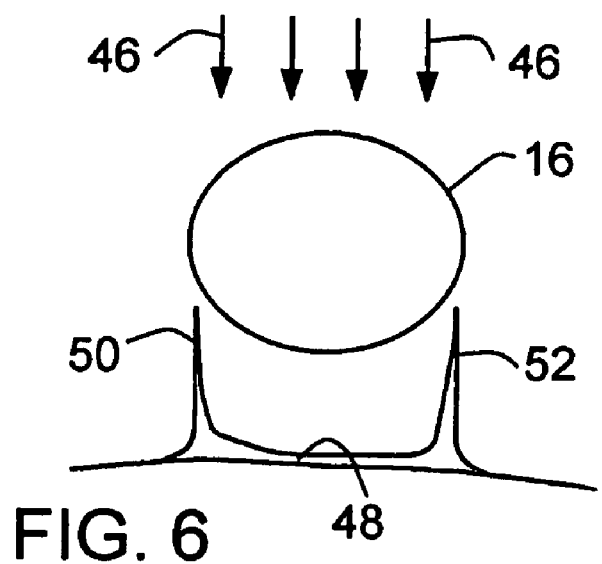
FIG. 6

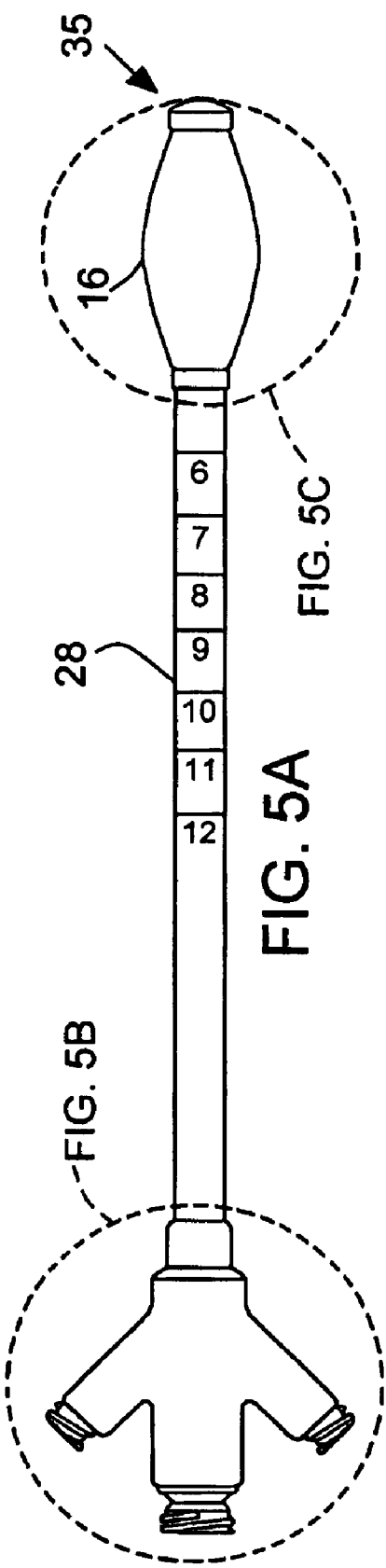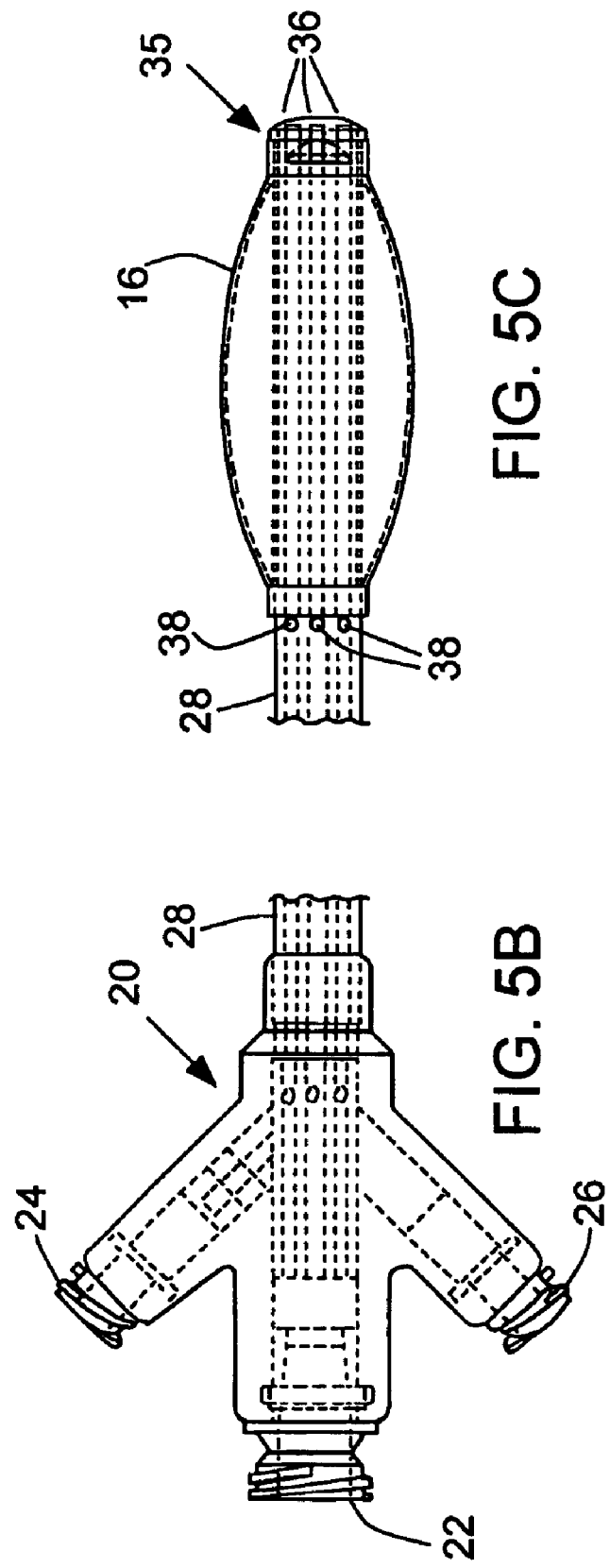

RADIATION TREATMENT USING X-RAY SOURCE

This application is a continuation in part of application Ser. No. 10/683,885, filed Oct. 10, 2003, now Pending.

BACKGROUND OF THE INVENTION

This invention concerns therapeutic radiation treatment of living tissue, usually but not necessarily within a body cavity, which may be a surgical cavity following a resection of a tumor. In one aspect the invention is concerned with use of a switchable, miniature electronic x-ray source, which may be controllable as to depth and intensity, for administering such therapeutic treatment.

Treatment of surgical cavities, such as after malignant tumor excision, has been accomplished with applicators which are inserted usually into a newly formed opening through the skin, a conveniently located opening into the surgical resection cavity. Generally the location is different from the surgical closure itself. Applicators have been disclosed which essentially comprise a balloon of known and relatively rigid geometry, essentially spherical, expandable generally to about four to six centimeters, that is, designed to have an inflated size of about four to six centimeters diameter. Some of the generally spherical balloon catheters were described as having multiple walls to form inner and outer spaces, for reasons relating to the objective of delivering a uniform dose to tissue surrounding the balloon. In the prior art such known-geometry balloons were inflated with a liquid, with an applicator guide positioned within the balloon and in the liquid, so that the applicator guide could receive a radiation source comprising a radioactive isotope.

With balloons limited to known geometries, there are limitations in the ability to treat a cavity margin thoroughly. In some cases, the patient cannot take advantage of such a treatment protocol because the known-geometry balloon applicator simply cannot fill many surgical cavities that are irregular in shape. Other measures have to be used in those cases, such as external radiation therapy.

Another limitation of known procedures using balloon catheters is in regard to locating the balloon correctly within a cavity of the patient, such as a resection cavity. The saline solution used to inflate the balloon contains contrast material which will be visible by taking an external x-ray. With the contrast material contained in the balloon's solution, the surgeon or technician can detect a pale "shadow" in the x-ray to determine the location of the balloon and to correct its position if needed. The procedure typically calls for use of the contrast material at about 3% in the saline solution. Dose planning for the known-geometry balloon is based on specific concentration of contrast. However, because the balloon shape is difficult to see in the x-ray, surgeons usually add the contrast material in a much higher concentration, not as contemplated by the dose plan, so as to better detect the balloon in the x-ray. The concentration may be up to about 20%-30% in practice. As a result, the therapeutic radiation from the x-ray source placed into the center of the balloon becomes attenuated to the extent that the actual dose profile received in a patient's tissue may be significantly less than the prescribed dose.

The use of isotopes has been the practice in administering x-ray radiation to patients prior to the present invention. The isotopes must be handled carefully and reliably shielded between uses. With the isotopes they are always "on", and only one setting is available for all dwell locations where a dose is to be administered. In many cases it would be convenient to have a better procedure and source that would allow modulation and more accurate dose delivery.

SUMMARY OF THE INVENTION

The invention now disclosed provides improved procedures for therapeutic radiation treatment of tissue, which may be following resection of a tumor or which may involve administering the radiation within an existing body cavity or in other locations. Although isotopes can be used in some of the procedures of the invention, in some, the radiation is emitted from an electronic switchable x-ray source that can be modulated as to dose depth, via voltage in the x-ray source, and preferably also as to intensity, via current in the x-ray source. In a preferred form the source is a miniature x-ray tube, having a diameter on the order of roughly about ½-3 mm, and a length of about 5-15 mm.

Pursuant to the invention a miniature x-ray tube is inserted into a balloon catheter, either before or after the balloon has been placed at the desired location in the patient. The x-ray source is switched on via a control unit outside the patient only when the balloon has been inserted, inflated and confirmed as to position, and with the patient and physician ready to administer the prescribed dose profile to the patient. Radiation dose delivery can be high compared to prior practice, about 5 to 50 Gy/hour. The x-ray source can operate in the range of about 40 kVp to 80 kVp.

In another aspect of the invention, either a switchable x-ray source or an isotope can be used in a therapeutic radiation treatment procedure. The balloon of the catheter is doped with contrast medium, in or on the skin of the balloon. The inflation medium for the balloon, which may be a saline solution, need not have any contrast medium added. The balloon catheter is placed in a cavity of living tissue, i.e. in a patient, and the balloon is inflated and then verified as to position in the cavity. This can be done by an x-ray taken exteriorly to the patient, since the balloon skin with contrast medium will have its outline visible by x-ray, after which the position of the balloon can be adjusted, if necessary. Once the correct balloon position has been verified by external imaging, the x-ray source, which may be an isotope source or a switchable source, is placed in the balloon catheter (if a switchable tube the source can be placed in the balloon before insertion). The source preferably is moved through a series of positions within the balloon catheter to administer radiation to tissue adjacent to the balloon, in accordance with a prescribed dose profile. This can be done in a series of iterations of placing the x-ray source and subsequently removing the source, for a series of dose fractions, over a treatment period that can extend over several days.

The use of a balloon catheter with contrast medium in or on the skin of the balloon, as opposed to being contained in a saline solution within the balloon, is a strong departure from the prior art. The advantage is that the physician will not over-dope the saline solution with contrast medium, thus maintaining the strength of the therapeutic radiation emitted from inside the balloon. The balloon wall has virtually no attenuating effect on the therapeutic radiation, when the radiation passes through the balloon in a normal or generally normal direction to the skin of the balloon. However, when the x-ray is taken from outside, the outline of the balloon will show up sharply because of the tangential direction of viewing that outline and the fact that the outline represents many times the wall thickness of the balloon, perhaps 20-40 times the density of contrast medium, thus contributing to the visible outline in the x-ray.

DESCRIPTION OF THE DRAWINGS

FIG. 1 shows a catheter device of the invention with an inflatable balloon applicator within which is an x-ray source, shown at a cutaway of the balloon.

FIG. 2 schematically shows the device of FIG. 1 with the balloon inserted in a cavity of a patient's body and inflated.

FIGS. 3 and 3A are a schematic elevation showing the device in a patient's breast; and a graph indicating modulation of dose depth for x-rays from a switchable x-ray source for the situation of FIG. 3 at different positions, in accordance with a dose prescription and taking into account adjacent organs and tissues.

FIGS. 4 and 4A are a schematic similar to FIG. 3; and a graph showing an aspect of dose modulation, in this case modulation of dose intensity by modulating current in the x-ray tube, for different positions as shown in FIG. 4.

FIGS. 5A, 5B and 5C show the catheter and the components of the catheter of the invention in greater detail.

FIG. 6 schematically indicates the balloon of the catheter in cross section, as it is x-rayed from the exterior of a patient, with a graph indicating generally the attenuation of x-rays as a function of position on the balloon.

DESCRIPTION OF PREFERRED EMBODIMENTS

Figure 7:
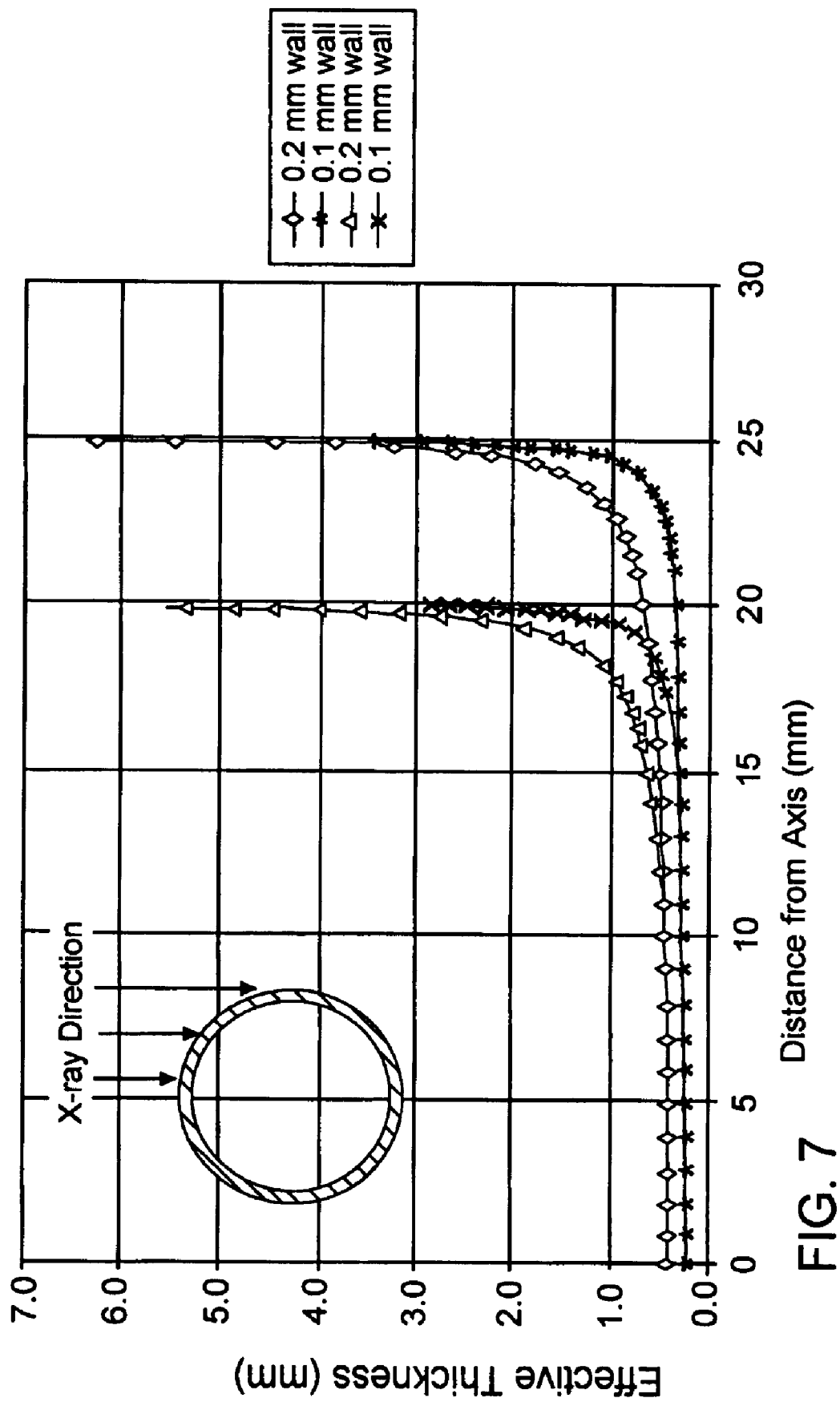
FIG. 7 is a graph indicating path length for x-rays passing through the balloon as in FIG. 7.

In the drawings, FIG. 1 shows somewhat schematically an applicator 10 according to one embodiment of the invention, the applicator including a flexible control line or cable 12 leading from a controller, not shown, and a catheter or applicator portion 14. A balloon 16 of the applicator and catheter is shown inflated in FIG. 1. The applicator device is generally as shown in co-pending application Ser. No. 10/683,885, filed Oct. 13, 2003.

As shown, at the proximal end 18 of the applicator is a branch 20. The three ports 22, 24 and 26 of this branch device may comprise a service port, a drainage port and a balloon inflation port, respectively. The functions of these ports are explained further below with reference to other drawings.

A flexible main shaft 28 extends from the branch device 20 to the balloon 16, and is sealed to the balloon at 30. The balloon in FIG. 1 is shown partially cut away to reveal an electronic x-ray source 32 within the balloon, at the end of the control line 12 and moveable longitudinally within the balloon 16 and catheter 10. In preferred embodiments the x-ray tube 32 is less than 4 mm in diameter, preferably no greater than about 3 to 3.2 mm in diameter, and in some embodiments this tube is as small as 1 mm in diameter or even smaller.

The shaft 28 is flexible, and may be highly flexible and pliable near the proximal end 18, as explained in the co-pending application referenced above, for the purpose of folding the applicator over against the breast when not in use, when the control line 12 and x-ray source 32 are not inserted into the applicator, particularly for breast irradiation involving several dose fractions such that the applicator need not be removed between fractions.

The flexible shaft provides a lumen for admitting a fluid to inflate the balloon 16, while also providing a duct or lumen for insertion of the radiation source 32, via guides connected to the balloon. The shaft 24 also preferably provides a channel for drainage of liquids from the body cavity within which the applicator is inserted. A drainage receptacle can be connected to the end of the drainage port or an aspirator can be used when needed to withdraw liquids. The applicator 10 is shown schematically in FIGS. 2, 3 and 4 as inserted into a resection cavity of a breast for treatment.

FIGS. 5A, 5B and 5C show the applicator 10 in greater detail, and with the balloon 16 deflated and collapsed. The service port 22, in line with the flexible shaft 28, as well as the drainage port 24 and the balloon inflation port 26, are illustrated. Also shown is a distance scale preferably included, with distances shown at 6 cm, 7 cm, 8 cm, etc., up to about 15 cm, to indicate to the physician the total depth of the applicator into cavity and opening wound. This provides a direct and easily used means to determine the position of the distal end 35 of the applicator as it is being inserted. As shown in FIGS. 5B and 5C, drainage is provided for the resection cavity via drain holes 36 at the distal end 35 of the applicator, beyond the balloon 16, communicating internally to the drain port 24, and also preferably via drain holes 38 shown just proximal of the balloon, for draining fluids which travel over the surface of the balloon. As in co-pending application Ser. No. 10/683,885, the balloon preferably has some form of liquid channeling means on its outer surface. This could be a multiplicity of bumps, allowing for liquid travel even though the balloon is engaged against the tissue, or a series of longitudinal ridges on the balloon surface to form channels. The drain holes 38 catch most of the liquid flowing in this manner, and these holes communicate with the drain port 24.

The balloon 16 may advantageously be formed of a silicone material, although other appropriate biocompatible materials can be used. The balloon material is bonded to the outside surface of the flexible shaft 28 in sealed relationship thereto, by known procedures.

FIGS. 2, 3 and 4 indicate somewhat schematically the use of the applicator device 10 in a resection cavity of a human breast 41, for radiation therapy. In FIG. 2 the catheter 10 is shown with its balloon 16 shown in dashed lines, and the shaft 28 in the balloon forming a guide for an x-ray source which may either be a miniature x-ray tube or an isotope. A seal 40 is shown in FIG. 2, for sealing the flexible shaft 28 of the catheter/applicator against the surface of the skin where it enters the body. Also shown in FIG. 2 is a connector 42 for connecting the applicator shaft, via the service port 22, to an exterior cable 44 that contains the control cable 12, leading to the controller (not shown) for the applicator and for the x-ray source, if the source is a controllable miniature tube.

FIGS. 3 and 3A illustrate the ability of the invention to achieve a more exact dose profile by use of a miniature electronic x-ray source in the applicator 10, a source which is capable of voltage variation and thus variation of the depth of dose. As one rather simple example, four dwell positions are shown in FIG. 3 and represented in a bar graph in FIG. 3A. The deepest dwell position, position 1, is closest to the lungs of the patient. Thus, the voltage is relatively low for this dwell position, controlling the depth of penetration into the surrounding tissue such that radiation will not reach the lungs to any appreciable degree.

The second dwell position is farther from the lungs, and FIG. 3A shows that the voltage is increased for this dwell position, for a greater depth of penetration. Similarly, dwell positions 3 and 4 are progressively farther from the lungs and the voltage and depth of dose are progressively higher.

FIGS. 4 and 4A illustrate schematically the use of a switchable, controllable electronic x-ray source in the catheter 10, wherein current is varied at different dwell positions in order to vary the dose intensity at different positions. In the schematic drawing of FIG. 4, four different dwell positions are again indicated for the electronic x-ray source, within the balloon 16 of the catheter 10, the balloon positioned in a resection cavity in a patient's breast 41. The control current does not vary the depth of penetration of the radiation, only the dose intensity. In the illustrated procedure, the current is varied in order to produce a uniform isodose profile. Thus, at positions 1 and 4 where the x-ray source is closest to tissue, the current is set at a lower level, while at dwell positions 2 and 3, close to the center of the balloon 16 and of the resection cavity, where the tube is more distant from tissue, the current is set higher. Note that dose intensity can be controlled also by controlling the length of time the source is "on" at each dwell position, or simply by controlling the length of dwell at each position assuming the source remains "on". These profiles of FIGS. 4 to 5A are just examples of how the variation of voltage and current using an electronic x-ray source can be beneficially used accurately to create a required isodose profile.

FIGS. 6 and 7 illustrate the balloon 16 having an x-ray contrast medium in or on the balloon wall. As explained above, this differs from prior practice in which a saline solution within the balloon contained a weak solution of contrast medium so that the balloon would show up in external x-ray imaging, for location of the balloon. In this case the contrast medium is only in or on the balloon wall, and this medium will absorb radiation, indicated at 46, during external imaging; it will also absorb radiation from the therapeutic source and thus will attenuate the radiation delivered from inside the balloon to some extent. However, with a low concentration of such contrast medium in the balloon wall, the attenuating effect of the medium for radiation passing through the balloon at an angle normal or generally normal to the balloon wall will be small and essentially negligible. On the other hand, the effect of radiation, particularly x-ray radiation, passing tangentially through the edges of the balloon as indicated in FIGS. 6 and 7, will be at a maximum, since the radiation must pass through the balloon edge wise at this tangential angle, a much longer effective path length. The result is that a balloon 16 with such contrast medium can be located by external x-ray, visible in an x-ray image by its edges. This is demonstrated in FIG. 7 showing effective path length of x-rays through balloon material as a function of distance from the center of the balloon. The densest outline of the balloon will be at its circumference, especially at distal and proximal ends of the balloon itself, where the wall material may be somewhat thicker at its attachment to the flexible shaft 28 and in any event, where the balloon has areas that are stretched far less due to the geometry of the balloon and its attachment to the flexible shaft 28 of the catheter device.

FIG. 6 shows in a schematic approximation a graph of x-ray density (darkness or density of the line appearing in an x-ray image) on a vertical axis, versus position. For clarity the balloon 16 is represented directly adjacent to the graph, and showing the direction of x-ray radiation 46. As illustrated, density is low in the x-ray image of the balloon at a region 48 in FIG. 6 where the radiation passes generally normally through the balloon wall; however, spikes of extreme density are shown at 50 and 52, where the rays must pass through considerable distance of the balloon wall on edge. As can be seen from the graph of FIG. 7 (showing effective path length through both 4 and 5 cm diameter balloons), the effective path length at these tangent regions can be about 15 to 25 times greater than the normal path length. Thus, the contrast-doped balloon wall provides a far superior imaging arrangement than the prior saline solution, without adversely affecting therapeutic radiation.

The procedures and apparatus described above are applicable to natural body cavities (e.g., bladder, uterus, vaginal), and naturally occurring lumens, as well as surgically created cavities. The term cavity in the claims is intended broadly to refer to natural or surgical cavities or lumens. Also, except where a switchable x-ray source is specifically called for herein for the advantages it offers in modulation or other purposes, the described procedures can ordinarily be performed using isotopes. The term brachytherapy device refers to either type of radiation source.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A method for irradiating living tissue using a balloon applicator, comprising:

placing the balloon applicator in a cavity of the living tissue, inflating the balloon applicator, and verifying the balloon placement by x-ray imaging taken exterior to the patient, the balloon applicator having a balloon wall adjacent to tissue to be irradiated, and the balloon wall being doped with x-ray contrast material, so that the imaging passes x-ray radiation tangentially through edges of the balloon and detects an outline of the balloon as a thin circle and the verifying of balloon placement is performed by detecting the thin circle outline of the balloon, positioning a switchable x-ray source at a desired position in the balloon applicator, and moving the source through a series of positions within the balloon applicator, to administer radiation to tissue adjacent to the balloon.

2. The method of claim 1, wherein the step of moving the switchable x-ray source comprises stepping the position of the x-ray source through a series of distinct dwell positions, and turning the x-ray source on at each dwell position and off between dwell positions.

3. The method of claim 1, further including modulating x-ray dose depth at different positions within the balloon applicator by adjusting voltage in the switchable x-ray source, and adjusting intensity of x-rays during the treatment in accordance with a dose prescription, as the source is moved through the cavity.

4. The method of claim 1, including a plurality of iterations of the steps of placing the x-ray source into the balloon applicator within the cavity and removing the x-ray source, for a series of dose fractions over a treatment period which may extend over several days.

5. The method of claim 1, wherein the balloon is generally spherical in shape.

6. The method of claim 1, wherein the balloon is generally ellipsoidal in shape.

7. The method of claim 1, wherein the balloon is generally hotdog shaped.

8. The method of claim 1, wherein the cavity in the tissue is irregularly shaped, and wherein the balloon is shaped to match the cavity.

9. The method of claim 1, including administering x-ray dose from the switchable x-ray source at about 5-50 Gy per hour.

10. The method of claim 1, wherein the switchable x-ray source is operated at greater than about 40 $kV_p$.

11. The method of claim 1, wherein the switchable x-ray source is operated at about 40 $kV_p$ to 80 $kV_p$.

12. The method of claim 1, wherein, during treatment using the switchable x-ray source, the x-ray source is modulated in intensity of radiation by modulating current in the x-ray source to accurately achieve a prescribed isodose profile.

13. The method of claim 12, further including modulating x-ray dose depth at different positions within the balloon applicator by adjusting voltage in the switchable x-ray source.

14. A method for irradiating living tissue using a balloon applicator, comprising:

placing the balloon applicator in a cavity of the living tissue, the applicator having a flexible shaft, and inflating the balloon applicator, positioning a switchable x-ray source in the flexible shaft and at a desired position in the balloon applicator, using a flexible, bendable cable with the x-ray source positioned at the end of the cable, the x-ray source being a miniature x-ray tube no greater than about 3.2 mm in diameter, switching on the x-ray source, and moving the source through a series of positions within the balloon applicator, to administer radiation to tissue adjacent to the balloon.

15. The method of claim 14, wherein the step of moving the switchable x-ray source comprises stepping the position of the x-ray source through a series of distinct dwell positions, and turning the x-ray source on at each dwell position and off between dwell positions.

16. The method of claim 14, wherein the step of moving the x-ray source comprises moving the source continuously while modulating radiation from the x-ray source by at least one of: (a) switching the x-ray source on and off, (b) varying current in the x-ray source to modulate dose intensity, and (c) varying voltage in the x-ray source to modulate x-ray dose depth at different positions.

17. The method of claim 14, further including modulating x-ray dose depth at different positions within the balloon applicator by adjusting voltage in the switchable x-ray source, and adjusting intensity of x-rays during the treatment in accordance with a dose prescription, as the source is moved through the cavity.

18. The method of claim 14, wherein the step of moving the switchable x-ray source comprises stepping the position of the x-ray source through a series of distinct dwell positions, and modulating radiation from the x-ray source at different positions by at least one of: (a) switching the x-ray source on and off, (b) varying current in the x-ray source to modulate dose intensity, and (c) varying voltage in the x-ray source to modulate x-ray dose depth.

19. The method of claim 18, including a plurality of iterations of the steps of placing the x-ray source into the balloon applicator within the cavity and removing the x-ray source, for a series of dose fractions over a treatment period which may extend over several days.

20. The method of claim 14, including a plurality of iteration of the steps of placing the x-ray source into the balloon applicator within the cavity and removing the x-ray source, for a series of dose fractions over a treatment period which may extend over several days.

21. The method of claim 14, wherein the balloon is generally spherical in shape.

22. The method of claim 14, wherein the balloon is generally ellipsoidal in shape.

23. The method of claim 14, wherein the balloon is generally hotdog shaped.

24. The method of claim 14, including administering x-ray dose from the switchable x-ray source at about 5-50 Gy per hour.

25. The method of claim 14, wherein the switchable x-ray source is operated at greater than about 40 $kV_p$.

26. The method of claim 14, wherein the switchable x-ray source is operated at about 40 $kV_p$ to 80 $kV_p$.

27. The method of claim 14, further including draining liquids from the cavity of the living tissue while the inflated balloon is within the cavity, using drain lumens formed in the applicator and extending to exterior of the tissue.

28. The method of claim 27, wherein the balloon wall has an exterior surface with texture to define drain channels to provide a path for flow of liquids toward the exterior of the cavity.

29. The method of claim 28, wherein the balloon applicator has a generally central flexible shaft having drain holes in a distal end of the shaft, distal of the balloon, connected to the drain lumens which pass through the shaft, and further including drain holes in the exterior of the shaft proximal of the balloon for collecting liquids traveling over the surface of the balloon.

* * * * *